US008816680B2

(12) United States Patent
LePage

(10) Patent No.: US 8,816,680 B2
(45) Date of Patent: Aug. 26, 2014

(54) EDDY CURRENT ARRAY CONFIGURATION WITH REDUCED LENGTH AND THICKNESS

(71) Applicant: Olympus NDT Inc., Waltham, MA (US)

(72) Inventor: Benoit LePage, Quebec (CA)

(73) Assignee: Olympus NDT Inc., Waltham, MA (US)

( * ) Notice: Subject to any disclaimer, the term of this patent is extended or adjusted under 35 U.S.C. 154(b) by 0 days.

(21) Appl. No.: 13/974,422

(22) Filed: Aug. 23, 2013

(65) Prior Publication Data

US 2014/0002072 A1    Jan. 2, 2014

Related U.S. Application Data

(62) Division of application No. 12/832,620, filed on Jul. 8, 2010.

(51) Int. Cl.
*G01N 27/72* (2006.01)
*G01R 33/12* (2006.01)

(52) U.S. Cl.
USPC ........................................... 324/239

(58) Field of Classification Search
USPC ........................................... 324/239
See application file for complete search history.

(56) References Cited

U.S. PATENT DOCUMENTS

| 3,495,166 A | 2/1970 | Lorenzi et al. |
| 5,389,876 A | 2/1995 | Hedengren et al. |
| 6,501,267 B1 | 12/2002 | Kurokawa et al. |
| 2005/0007108 A1 | 1/2005 | Dogaru |

*Primary Examiner* — Reena Aurora
(74) *Attorney, Agent, or Firm* — Ostrolenk Faber LLP

(57) ABSTRACT

The invention herein disclosed provides a 2D coil and a method of using the 2D wound EC sensor for reproducing the Eddy Current Testing (ECT) response of a prior art 3D orthogonal sensor. The resulting thin-film eddy current array of coils configured to be placed parallel and against the test surface, and a corresponding eddy current circuitry operable to excite and receive eddy current from the array of coils. The array of coils forming at least a first inspection channel and a second inspection channel. The eddy current circuitry is configured and operable in a way that the one of the first pair of driver coils is usable as one of the second pair of driver coils; and one of the first pair of receiver coils is useable as one the second pair of receiver coils.

7 Claims, 4 Drawing Sheets

EDDY CURRENT ARRAY CONFIGURATION WITH REDUCED LENGTH AND THICKNESS

CROSS-REFERENCE TO RELATED APPLICATIONS

This application claims the benefit and priority and is a divisional continuation application of U.S. patent application Ser. No. 12/832,620 filed Jul. 8, 2010 entitled A 2D COIL AND A METHOD OF OBTAINING EC RESPONSE OF 3D COILS USING THE 2D COIL CONFIGURATION, the entire disclosure of which is incorporated herein by reference.

FIELD OF THE INVENTION

The present invention relates to non-destructive testing and inspection systems (NDT/NDI), particularly to a method of emulating eddy current (EC) fields generated by a 3D coil using a 2D coil configuration which can be fabricated on a printed circuit board (PCB).

BACKGROUND OF THE INVENTION

EC inspection is commonly used in NDT/NDI applications to detect flaws in surfaces of manufactured components fabricated out of conductive materials, such as steel bars, tubes and pipes. EC is often used to inspect components for automotive, aeronautic and energy industries. Over the years, EC sensors have been designed with different configurations and patterns to suit for different applications.

Various EC systems have heretofore been provided for the detection of cracks and or other flaws in a part under test. In general, such systems include field producing means such as a coil connected to an AC source to generate EC's in a part and a sensing means to sense the field produced by the EC's. The sensing means may be a separate coil, a Hall probe, or any other field responsive device, or the coil of the field-producing means may also be used to sense the EC-induced field, by measuring the effective impedance thereof In such prior systems, difficulties are encountered due to the changes in conductivity and permeability of the part under test and also due to the variations in spacing between the test coil or probe and the surface of the part, and variation in surface conditions. It has been possible to reduce the effect of variations in spacing by certain arrangements such as by the use of impedance networks and by adjustment of operating frequency. Such arrangements, however, have not overcome the sensitivity to conductivity and permeability changes. To reduce the effect of conductivity and permeability changes, differentially connected coils have been used. However, such arrangements have been insensitive to defects common to the differentially connected coils.

Background art has evolved over the years with the general object of overcoming the disadvantages described above for EC testing systems and providing systems which are very sensitive to defects while being insensitive to variations in other physical characteristics of a part under test and variations in the physical relation of a test probe to the part. U.S. Pat. No. 3,495,166 is incorporated by reference as the example for background art described below.

In accordance with an important feature of the background art, an EC system is provided which includes field-sensing means for sensing fields produced by EC's in two regions having substantially the same spatial relation to a surface of the part and having a substantial angle there between with detector means being provided for detecting differences between the fields produced in the two regions. It should be noted that the sensing regions of the field-sensing means are orthogonal to the emitted magnetic field regions of field-producing means. Accordingly, in the absence of a defect that will disrupt the direction of the EC flow imparted by the field-producing means, the magnetic field resulting from the EC flow will also be orthogonal to the field-sensing means and will consequently not be sensed. With this arrangement, a high degree of sensitivity is obtained with respect to flaws having different orientations with respect to the sensing regions, while being insensitive to changes in a) conductivity, b) permeability, c) irregular surface finishes and d) to changes in the spacing of the part. This insensitivity stems from the fact that properties a, b, c and d affect predominantly the magnitude of the EC flow and resulting magnetic field, but not the direction.

It is found that almost all defects which are of interest in the testing of a part have a dimension which is greater in one direction than in another and with a substantial angle being provided between the sensing regions, a high degree of sensitivity to significant types of defects is obtained. At the same time, the sensing regions can be quite close together so as to obtain extremely low sensitivity to variations in spacing or surface conditions, while also obtaining very low sensitivity to changes in conductivity and permeability.

According to another important feature of the background art, the sensing regions are crossed to intersect at mid-points thereof so that the area of the part which is inspected is minimized and so that the sensing regions always have the same physical relationship to the part being inspected.

According to a specific feature of the background art, the angle between the sensing regions is approximately 90 degrees, to obtain maximum sensitivity to defects.

According to another specific feature of the background art, the sensing regions are relatively long and narrow with transverse dimensions equal to a small fraction of the long dimension thereof, to obtain high resolution and to facilitate detection and location of narrow cracks within a part.

In accordance with a further feature of the background art, a pair of coils are used which are located in planes generally transverse to the surface of the part.

In certain of the arrangements according to the background art, the pair of coils are used as part of the field-producing means by connection thereof to an AC source. The same coils may be used as part of the sensing means, or may be used only in the sensing means with another coil or coils being used in the field-producing means. In one arrangement, the field-producing means comprise a coil having an axis generally parallel to a line at the intersection of the planes of a pair of coils used in the sensing means.

In accordance with an important feature of the background art, the coils have matched inductances and resistances, to obtain an accurate balance and to minimize sensitivity to conductivity and permeability variations and sensitivity to changes in the spacing between coils and the test part.

In one arrangement in which the same pair of coils are both used in field-producing and field-sensing means, a bridge circuit is provided having two branches each having two legs with the two branches being connected to an AC voltage source. The pair of coils forms two legs of the bridge circuit while impedance means form the other two legs of the bridge circuit and detector means are provided connected between the junction of the legs of one of the branches and the junction of the legs of the other of the branches. This arrangement further facilitates the attainment of an accurate balance and minimizes sensitivity to conductivity and permeability changes and changes to spacing.

With only one pair of coils, it is possible to miss defects located exactly along an angle intersecting the angle between the coils. Although this deficiency is not usually serious, it can be obviated by the provision of a second pair of coils in planes generally transverse to each other and at angles to the planes of the first pair of coils.

The 3D orthogonal sensor topology described above provides many benefits; however, a few drawbacks have been known to bring limitations to its usage. One such drawback is that, with coils wound onto a cube or cross-shaped core, the sensor is inevitably bulky, which limits the space it can access during inspections. Another drawback is that the fabrication of this sensor largely depends on having the coils manually wound onto the cubes or the cross-shaped cores. The fabrication is labor intensive and costly.

With the advances of printed circuit board (PCB) technologies over the last decades, it is now possible to manufacture some EC sensors with certain coil configurations on a thin, sometimes flexible, support. Significant benefit with the use of PCB technologies to manufacture EC array probes include reduced manufacturing cost, increased sensor flexibility and increased reproducibility. An example of such a probe is described in U.S. Pat. No. 5,389,876.

A drawback of currently available EC sensors or probes made from printed circuit boards is that they are limited to simply mapping the two-dimensional (2D) shape of the prior art coils that are wound on a plane that is approximately parallel to the inspected surface. This is because the printed circuit board is essentially a 2D structure. However, challenges remain in PCB manufacturing for some coil configurations such as used in the orthogonal sensors with a 3D structure.

The use of solid state magnetic field sensors such as anisotropic magnetoresistance (AMR) and giant magnetoresistance (GMR), combined with the printed circuit board technologies, made it possible to obtain probes with EC responses similar to the conventional orthogonal sensor. An example of this is shown in a patent publication US2005-0007108. In this publication, a flat winding coil generates ECs in the component under test while a GMR field sensor array picks up the orthogonal magnetic field generated when a defect disturbs the ECs. While this technology benefits some applications, it is unable to provide a fully flexible probe because the AMR and GMR sensors are discrete components on the PCB. There are also many limitations intrinsic to AMR and GMR sensors such as the risk of saturation and the need for magnetic biasing, both of which presents undesirable concerns in an industrial environment.

Accordingly, it is desirable to provide a method for emulating the EC effect of a 3D EC sensor structure using a 2D winding configuration, which is suitable to be fabricated using the current printed circuit board technologies.

It would also be desirable to provide a means for building an EC array probe including sensors that behave in the manner described for the 3D orthogonal background art sensors with the printed circuit board technology.

SUMMARY OF THE DISCLOSURE

As used herein, the term "3D EC sensor" is an EC sensor comprised of a magnetic field-producing and field-sensing means employed to respectively induce an EC flow in a test object surface and/or sense the response field thereof. The magnetic field-producing and field-sensing means of the 3D EC sensor are coils, orthogonally disposed or otherwise protruding with respect to the test object surface. The EC flow pattern produced on a planar test object surface by the field-producing means of the 3D EC sensor is comprised of adjacent regions with their respective EC flows in opposite directions. Furthermore, the term "2D EC sensor" should be construed to mean a magnetic field-producing and/or field-sensing means with similar properties as described above for the 3D EC sensor except that the field-producing and field-sensing means are disposed in a coplaner manner or in close proximity parallel planes such that it can be achieved by the use of conventional printed circuit board (PCB) technology.

It is an object of this invention to provide a method for emulating the EC response of a 3D EC sensor structure using a 2D coil or winding configuration which is suitable for being fabricated using technologies involving printed circuit board. The 3D EC sensor structure involves at least a portion of the EC coils that are un-parallel to the surface under inspection.

It is a further object of the present invention to provide a 2D EC sensor to emulate defect patterns nearly identical to its 3D orthogonal counterpart when used to inspect the target surface.

The method herein disclosed makes it possible to use 2D wound EC sensors to obtain defect signatures in the impedance plane very similar to, if not identical with, those obtained from their conventional 3D counterparts.

The significant benefit of the herein disclosed 2D sensor includes largely reducing the cost associated with manufacturing when using the 2D wound EC sensor to replace its 3D counterpart.

Other advantages inherently provided by the herein disclosed 2D wound EC sensors include being able to fabricate using PCB technologies, manufacturing with a fully automated process as compared to manually for its 3D counterpart, and having sensors that are very thin, mechanically flexible, if necessary, and easy to be used to access tight spaces for inspection.

Another advantage of the herein disclosed 2D EC sensor is that it allows the configuration of adding plurality of layers of such sensors to provide scanning with higher resolution.

Yet another advantage of the disclosed 2D sensor is that superior coupling is obtained between the herein disclosed sensor and the test surface which provides an increased signal strength.

BRIEF DESCRIPTION OF THE DRAWINGS

FIG. 1b is a perspective view of a basic embodiment illustrating the method of how to use 2D coil wound on a plane parallel to the test surface according to the present disclosure, with the generated EC flow imitating its 3D counterpart shown in FIG. 1a.

FIG. 2b is a perspective view of the presently disclosed 2D coil in a driver-pickup embodiment wound on a plane parallel to the test surface, with the EC effect imitating its 3D counter part shown in FIG. 2a.

DETAILED DESCRIPTION OF THE INVENTION

Figure 1A:
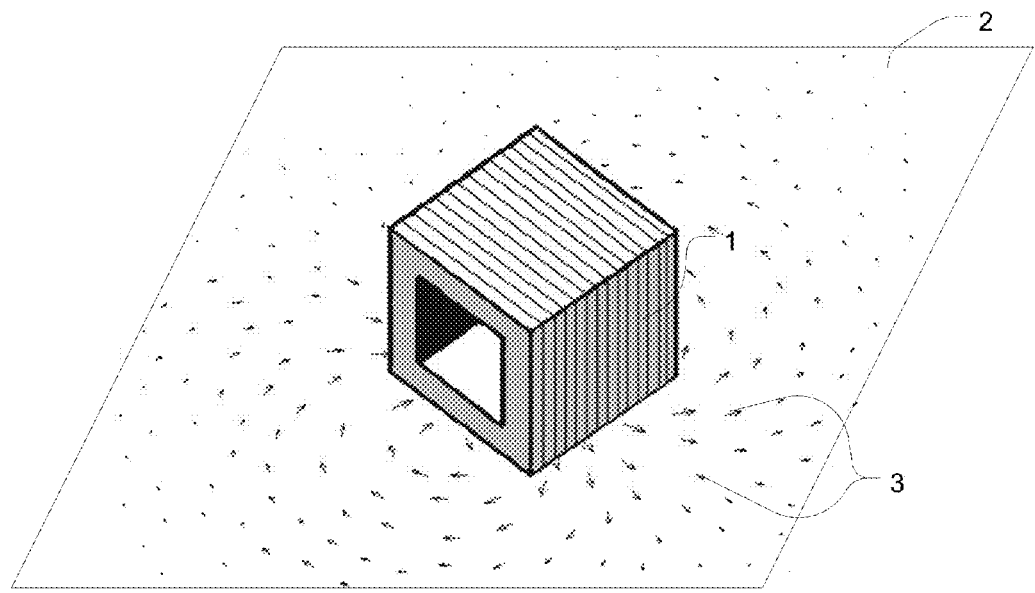
FIG. 1a (Prior Art) shows a conventional cubic orthogonal 3D coil along with a representation of the EC flow generated by the 3D coil onto a test surface.

FIG. 1a shows an EC flow 3 induced on a conductive test surface 2 by a conventional 3D EC drive coil 1. As can be seen, the driver coil 1 is wound on a 3D cubic core and the winding path includes two planes perpendicular to surface 2. In general, if EC drivers are wound on a winding plane parallel to the test surface, the induced EC flow on the test surface is parallel to the driver coil. For the case of the 3D EC drive, drive coil 1 is wound on a 3D structure that contains planes that are erected from (not parallel to) the test surface, whereas EC flow 3 is confined within test surface 2. EC flow 3 can therefore not always be parallel to driver coil 1. Instead, EC flow 3 is driven by the interaction between surface 2 and the magnetic flow generated by the driver 1 at surface 2 and forms a pair of whirls on surface 2 as shown in FIG. 1a.

Figure 1B:
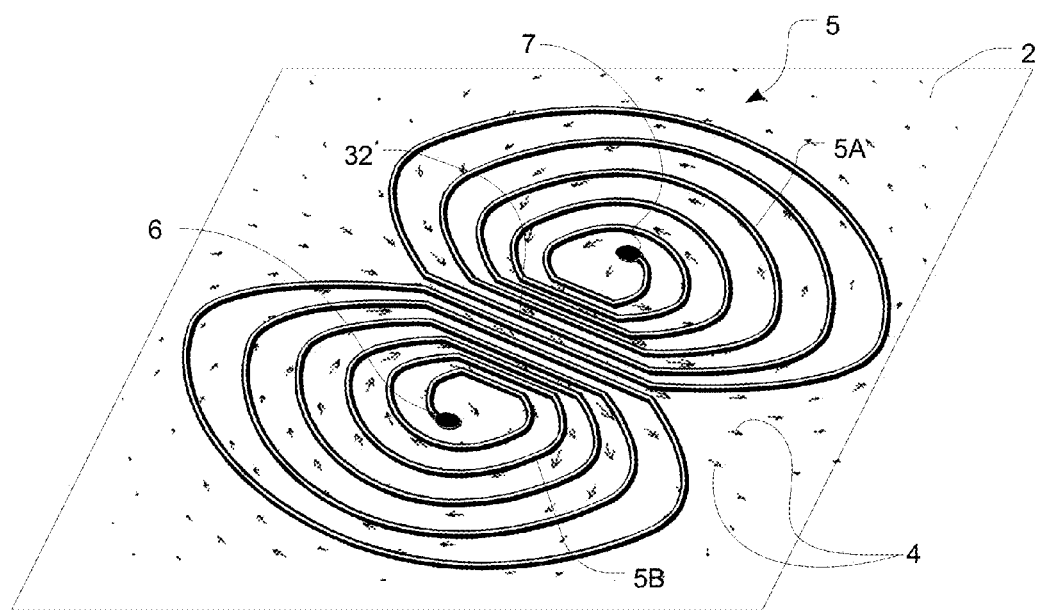

Referring now to FIG. 1b, a basic embodiment of the present disclosure is shown to include a pair of whirl-shaped 2D coil wound on a plane parallel to test surface 2 with the generated EC flow 4 conforming to the EC flow 3 of its 3D counterpart shown in FIG. 1a. In this embodiment, EC flow 4 is created using a flat 2D shaped coil 5 built on a plane parallel to the surface 2. It is apparent that EC flow 4 closely resembles EC flow 3 of FIG. 1a. Coil 5 is built in a pair winding 5A and 5B, being oppositely wound, with the look similar to the pair of whirl EC flow 3 shown in FIG. 1a.

Continuing with FIG. 1b, commercially available simulation tools are first used to compute the EC flow generated by conventional coil 1. The flat 2D winding pattern for coil 5 is then drawn knowing that the induced EC flow 4 will be substantially parallel to and following coil winding 5. Taking note that coil 5 includes two half-windings 5A and 5B, which are identical in shape but wound in opposite directions. Alternately, half-windings 5A and 5B may be wound in the same direction and be driven independently with a 180 degree phase difference in current to achieve the same effect. This independent drive method may be employed on a plurality of half-winding pairs such as those described later herein with reference to FIGS. 3 and 4.

As can be seen, a higher EC density can be achieved by increasing the winding density of winding coil 5, particularly as shown in area 32. With the same principle, it is feasible to shape EC flow 4 in order to reproduce, on surface 2, EC flow 3 that was generated by conventional coil 1.

It is important to note at this point that the goal of the present invention is to use 2D coils to emulate the EC flow distribution on surface 2 generated by a 3D coil arrangement. However, that is not to say that the same EC density magnitude is regenerated using the 2D coils. In other words, EC flow 4 is a scaled version of EC flow 3. Only a portion of the magnetic field generated by 3D coil 1 intersects with surface 2 while a much larger portion of the EC flow generated by 2D coil 5 intersects with surface 2 because they are much closer to it. This is a desirable feature of the 2D probe of the present invention since it increases the signal strength and thus potentially provides a better signal to noise ratio.

Still referring to FIG. 1b, as can be seen, coil 5 can be etched on a flexible or rigid printed circuit board (PCB) with widely used PCB technologies. Coil terminals 6 and 7 provide means for connecting the coils to an EC system acquisition unit (not shown) through separate PCB layers or by using soldered wires.

Another important aspect of this invention is that a 2D winding configuration such as the one used in coil 5 that emulates a driver coil such as coil 1 can also be used to emulate a receiver coil with the same principle disclosed above. In other words, a 2D winding pattern such as used in coil 5 can also be used to emulate the readings of a 3D receiver coil whose windings are set on 3D core such as in coil 1.

The geometric characteristics of the 2D flat winding pattern of the present invention can be determined by first ascertaining the pattern and direction of EC flow 3 resulting from incident magnetic field on a defect free surface 2 that is generated by the 3D driver coil that is the objective to emulate. After this pattern and direction are known, coil 5 shown in FIG. 1b is realized by having its windings conform to the shape and direction of EC flow 3.

It is widely known that a 3D coil configuration shown as in FIG. 1a can be used as an "absolute configuration", which serves both as a drive and a receiver. It is therefore conceivable that, according to the presently disclosed invention, one can use winding coil 5 shown in FIG. 1b both as a driver and a receiver in an absolute configuration to perform inspection for surface 2 and obtain an EC reading emulating the response of coil 1 that is also used in absolute configuration.

Figure 2A:
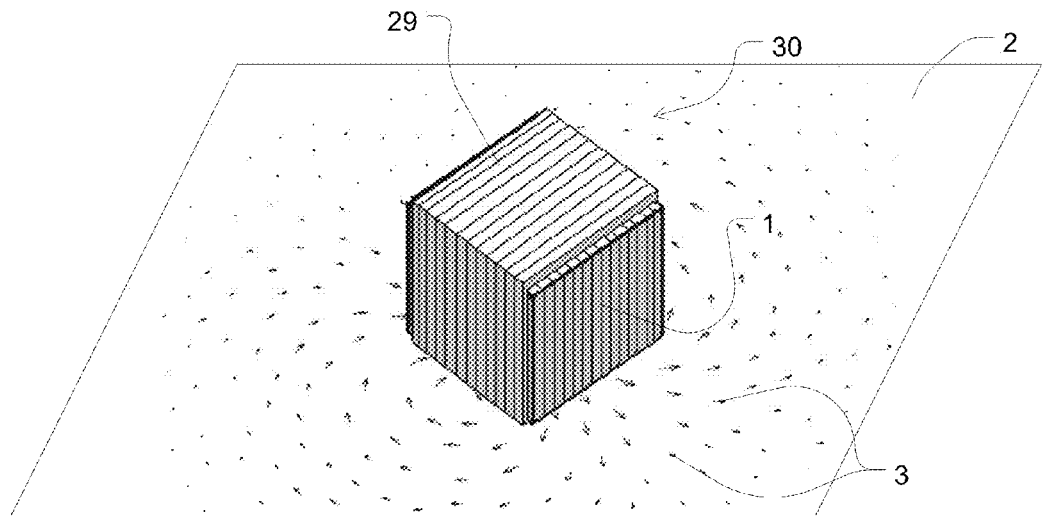
FIG. 2a (Prior Art) shows a conventional cubic orthogonal 3D sensor in a driver-pickup configuration along with a representation of the EC generated by this sensor onto the test surface.

Turning now to FIG. 2a, a type of a known orthogonal sensor 30 is seen involving separate driver coil 1 and receiver coil 29 for inspecting surface 2. As can be seen, receiver coil 29 is orthogonal to driver coil 1. Part of receiver coil 29 is perpendicular to test surface 2 plane onto which EC flow 3 is induced. Using the method herein disclosed and knowing that driver coil 1 and receiver coil 29 are almost identical in shape and number of windings but perpendicular to each other, an equivalent 2D flat winding configuration can be provided by employing two perpendicular coils shaped as coil 5 in FIG. 1b.

Figure 2B:
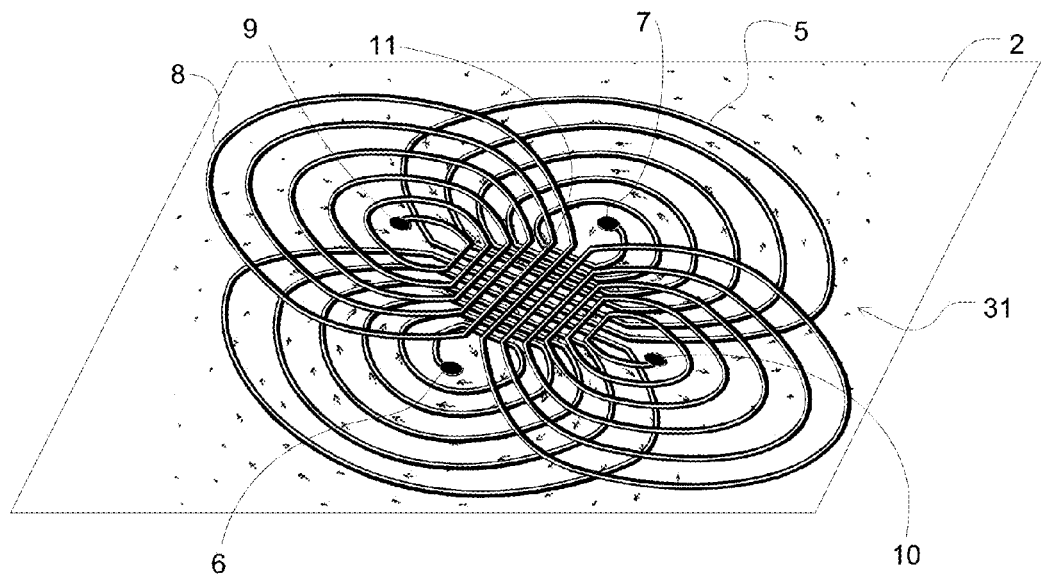

As shown in FIG. 2b, a 2D orthogonal sensor 31 embodies 2D coil 5 as driver and 2D coil 8 as the orthogonal receiver. Multilayer PCB technology allows sensors such as 31 to be manufactured on a single flexible or rigid PCB assembly by layering the driver and receiver windings on separate layers and by using the multilayer assembly to connect on winding leads 6, 7, 9 and 10. As such, the embodiment shown in FIG. 2b, a 2D orthogonal driver-receiver pair can be used to replace the conventional 3D orthogonal driver-receiver EC sensor shown in FIG. 2a.

It is worth noting that orthogonal coil configurations such as 30 and/or 31 are sensitive particularly within a small area 11 at the center on the probes. The actual width of this area is preferably defined as being no more than half of the diagonal of conventional coil 30. For such configurations wherein a small portion of the EC flow is responsible for the majority of the EC response, it is not as important to precisely match the EC pattern over the whole surface 2. With such consideration, the 2D orthogonal coil winding can therefore be modified to a simplified winding pattern as shown in FIG. 3.

Figure 3:
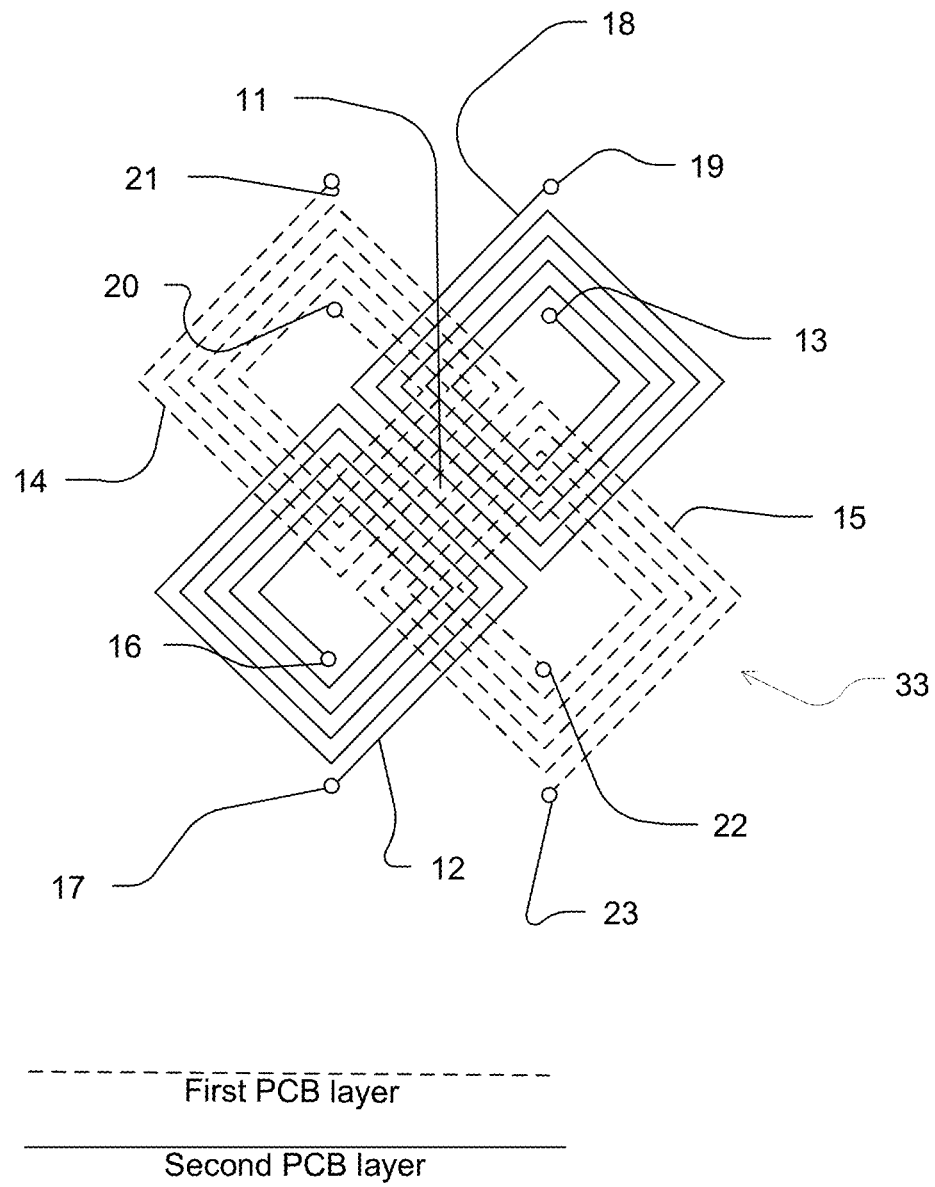
FIG. 3 illustrates a simplified winding embodiment using the presently disclosed 2D coil and reproducing the EC response of an orthogonal 3D driver-pickup sensor.

As shown in FIG. 3, the alternative 2D orthogonal coil winding is employed in coil 33. Noting that squared shaped coils 33 are used in lieu of ear-shaped coils as used in sensor 31 of FIG. 2b to simplify the design and manufacturing process. Geometries other than square may be used. Being only a rather rough approximation of the winding pattern of sensor 31, sensor 33 produces an EC response on the test surface substantially close to that produced by sensor 31. This is mainly due to the substantial equivalence in sensitive area 11 in both sensors 31 and 33.

Continuing with FIG. 3, it should be noted that sensor 33 includes four individual coils. In order to obtain a response equivalent to 3D orthogonal sensor 30 (in FIG. 2a), leads 13, 16, 20 and 22 must be connected to ground. Leads 19 and 17 are connected to the same driver signal (same amplitude and phase). Leads 21 and 23 are connected to a differential input to provide a single receiver signal. The benefit of this alternate method for connecting these windings will become apparent when considering the following disclosed array version of the flat orthogonal sensor.

Figure 4:
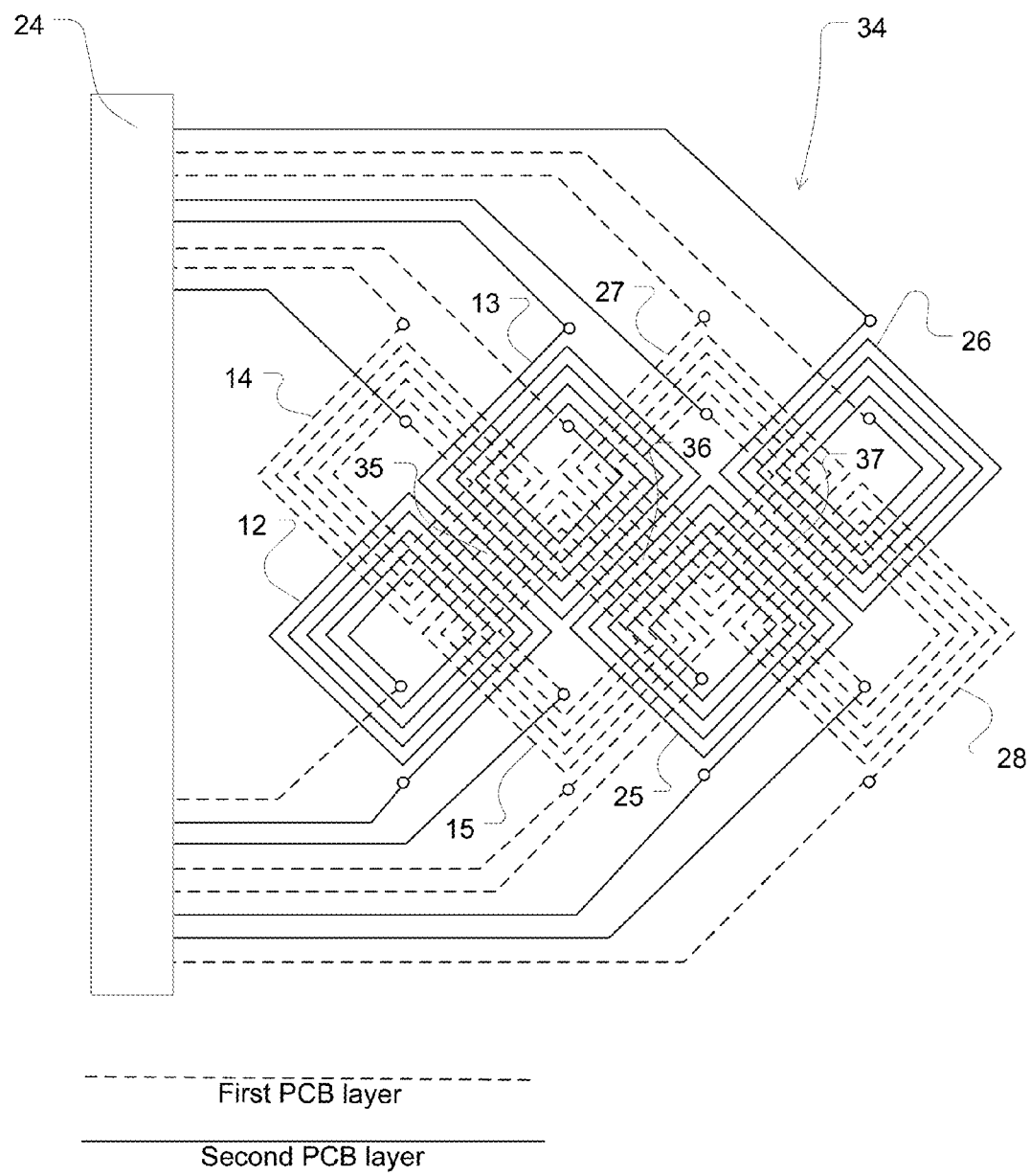
FIG. 4 shows a three channel EC array probe embodiment using a multi-layer 2D coil based on the winding method shown in FIG. 3.

Reference now is made to FIG. 4. In FIG. 4, array probe 34 comprises a coil configuration for building a compact EC array probe using multiple 2D coils as disclosed above in association with FIGS. 2b and 3 to reproduce the EC response generated by a 3D EC array probe. More specifically, probe 34 includes four 2D driver coils (12, 13, 25 and 26) and four 2D receiver coils (14, 15, 27 and 28). Multiplexer unit 24 can activate each driver winding and the corresponding pairs of receiver windings (14-15; 27-15; 27-28) sequentially. As seen in FIG. 4, the first inspection channel is generated by activating drivers 12 and 13 along with receivers 14-15 and provides a sensitive spot 35. The second inspection channel is generated by activating driver 13 and 25 along with receivers 27-15 and provides a sensitive spot 36. The third inspection channel is generated by activating driver 25 and 26 along with receivers 27-28 and provides a sensitive spot 37.

The above exemplary 2D EC array probe 34 shown in FIG. 4 is a three channel array probe. It should be noted that that any number of channels can be used to build such an array probe depending on the application.

Since multiplexer unit 24 and an acquisition unit (not shown) capable of supporting array probes such as 34 are commercially available, their details are therefore not elaborated here. It must also be understood that the two-layer PCB structure disclosed herein is exemplary. More layers of PCB design can also be used. For example, each coil could make use of several layers of PCB to increase the probe inductance which allows the use of lower test frequencies. Another example would be to stack several staggered probes such as 34 over the multi-layer structure to provide a better coverage (higher resolution) of the inspected surface.

Yet another example would be to use different PCB layers for detecting defects of different orientations by using an adapted coil pattern.

It should be further noted that, since it is known that conventional 3D orthogonal sensors can by connected in transmit-receive or in differential configurations, it is conceivable that the presently disclosed 2D orthogonal counterpart can likewise be connected in a differential configuration to provide a sensitivity axis shifted by 45 degrees, and that a corresponding array probe configuration can also be made.

As herein disclosed that equivalent windings, such as 5 in FIGS. 1b and 2b, or sets of windings such as 12 and 18 in FIG. 3, can be found to emulate any coils included in a given 3D sensor by obtaining equivalent EC patterns on the inspected surface as described in this invention, it is within the scope of the present invention that a wide range of coil configurations designed for the 3D sensors may be replicated with its 2D counterpart. The key is that the herein disclosed 2D flat sensors have the capability to provide an equivalent EC response on the surface being inspected and thus emulate the defect signatures as provided by the 3D counterpart in the impedance plane.

It is also important to note that coils 5A and 5B in FIG. 1b have substantially the same pattern. However, if driver/receiver coils to be emulated are of irregular patterns or are situated on the test surface asymmetrically, the EC flow resulting from the 3D coils will be of asymmetrical irregular patterns. The scope of the present disclosure pertains to the pattern of the EC flow generated by the 3D coils which are further used to determine the pattern of the 2D coils.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. An eddy current array probe assembly configured to perform eddy current inspection of a test object with a test surface, the assembly comprising:
   a thin-film eddy current array of coils configured to be placed parallel and against the test surface, and a corresponding eddy current circuitry operable to excite and receive eddy current from the array of coils, the array of coils forming at least a first inspection channel and a second inspection channel,
   wherein the first inspection channel further comprising a first pair of driver coils and receiver coils, wherein centers of the first pair of driver coils form a first driver sensitivity area and centers of the first pair of receiver coils form a first receiver sensitivity area; wherein, in a plan view taken in a direction towards the test surface, the first driver sensitivity area and the first receiver sensitivity area cross and are orthogonal to each other;
   wherein the second inspection channel further comprising a second pair of driver coils and receiver coils, wherein centers of the second pair of driver coils form a second driver sensitivity area and centers of the second pair of receiver coils form a second receiver sensitivity area; wherein, in a plan view taken in a direction towards the test object, the second driver sensitivity area and the second receiver sensitivity area cross and are orthogonal to each other;
   wherein the eddy current circuitry is configured and operable in a way that the one of the first pair of driver coils is usable as one of the second pair of driver coils; and one of the first pair of receiver coils is useable as one the second pair of receiver coils.

2. The eddy current array probe assembly in claim 1, wherein the first pair of driver coils are a pair of substantially identical, yet reversely wound driver coils and the first pair of receiver coils comprising a pair of substantially identical, differentially connected receiver coils; and,
   wherein the second pair of driver coils are a pair of substantially identical, yet reversely wound driver coils and the second pair of receiver coils comprising a pair of substantially identical, differentially connected receiver coils.

3. The eddy current array probe assembly in claim 1, wherein the eddy current circuitry is configured to excite the first pair of driver coils to cause an eddy current flow in the test object to be in a pattern of a pair of substantially identical yet reversely wound swirls; and,
   the eddy current circuitry is configured to excite the second pair of driver coils to cause an eddy current flow in the test object to be in a pattern of a pair of substantially identical yet reversely wound swirls.

4. The eddy current array probe assembly in claim 1, wherein the first pair of driver coils and receiver coils are over-laid on top of each other and the second pair of driver coils and receiver coils are over-laid on top of each other.

5. The eddy current array probe assembly in claim 1, wherein the array of coils is of a type fabricated using printed circuit board manufacturing technologies.

6. The eddy current array probe assembly in claim 1, wherein each of at least some of the array coils comprises at least first and second separate coil portions, each portion being wound in the same direction, driven independently with a 180 degree phase difference, the two coil portions being disposed on the same plane parallel to the test surface.

7. The eddy current array probe assembly in claim 1, wherein the array coils are formed by employing one of the array coils multiplied into a plurality of identical 2D coils arranged in a staggered manner in a series and/or in multiple layers.

* * * * *